(12) United States Patent
Motoyama

(10) Patent No.: US 9,675,521 B2
(45) Date of Patent: Jun. 13, 2017

(54) PROCESS FOR PRODUCING DRUG-BLOCK COPOLYMER COMPOSITE AND PHARMACEUTICAL PREPARATION CONTAINING SAME

(75) Inventor: Jun Motoyama, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 317 days.

(21) Appl. No.: 13/818,997

(22) PCT Filed: Aug. 31, 2011

(86) PCT No.: PCT/JP2011/069709
§ 371 (c)(1),
(2), (4) Date: Apr. 24, 2013

(87) PCT Pub. No.: WO2012/029827
PCT Pub. Date: Mar. 8, 2012

(65) Prior Publication Data
US 2013/0209390 A1    Aug. 15, 2013

(30) Foreign Application Priority Data

Sep. 2, 2010 (JP) ................................. 2010-196533

(51) Int. Cl.
| | |
|---|---|
| A61J 3/02 | (2006.01) |
| A61K 9/14 | (2006.01) |
| A61K 9/16 | (2006.01) |
| A61K 47/48 | (2006.01) |

(52) U.S. Cl.
CPC ............. *A61J 3/02* (2013.01); *A61K 9/1641* (2013.01); *A61K 47/48215* (2013.01)

(58) Field of Classification Search
CPC .... A61J 3/02; A61K 47/48215; A61K 9/1641
See application file for complete search history.

(56) References Cited

U.S. PATENT DOCUMENTS

| | | | |
|---|---|---|---|
| 5,449,513 A | 9/1995 | Yokoyama et al. | |
| 2003/0054036 A1* | 3/2003 | Liggins et al. | 424/486 |
| 2006/0057219 A1 | 3/2006 | Nagasaki et al. | |
| 2008/0113028 A1* | 5/2008 | Shimizu et al. | 424/486 |
| 2010/0129459 A1 | 5/2010 | Kwak et al. | |

FOREIGN PATENT DOCUMENTS

| | | | |
|---|---|---|---|
| CN | 1655763 A | 8/2005 | |
| CN | 101657190 A | 2/2010 | |
| EP | 1127570 A2 | 8/2001 | |
| EP | 2436377 A2 | 4/2012 | |
| JP | 6-206815 A | 7/1994 | |
| JP | 7-41154 A | 5/1995 | |
| JP | 2777530 B2 | 7/1998 | |
| JP | 11-114027 A | 4/1999 | |
| JP | 2003-12505 A | 1/2003 | |
| JP | 2003-342168 A | 12/2003 | |
| JP | 3615721 B2 | 2/2005 | |
| JP | 2006-516548 A | 7/2006 | |
| JP | 2010-524924 A | 7/2010 | |
| WO | 97/10849 A1 | 3/1997 | |
| WO | 02/072150 A2 | 9/2002 | |
| WO | 2004/060346 A2 | 7/2004 | |
| WO | 2005/007136 A1 | 1/2005 | |
| WO | 2006/033296 A1 | 3/2006 | |
| WO | 2008/130158 A1 | 10/2008 | |
| WO | 2009/040818 A1 | 4/2009 | |

OTHER PUBLICATIONS

Oxford Dictionary, "spray-dry", Oxford University Press, 2015, pp. 1-3 [online], [retrieved on Oct. 28, 2015], retrieved from the internet: <URL: http://www.oxforddictionaries.com/us/definition/american_english/spray-dry>.*
International Search Report and Written Opinion mailed Nov. 22, 2011 in corresponding PCT application No. PCT/JP2011/069709.
Japanese communication, with abridged English translation, mailed Jan. 20, 2015 in corresponding Japanese patent application No. 2012-531907.
Journal of Controlled Release, vol. 72, No. 1-3, 2001, pp. 191-202, "In vivo evaluation of polymeric micellar paclitaxel formulation: toxicity and efficacy", Kim, et al.
European Communication dated Feb. 6, 2014 in corresponding European patent application No. EP 11821842.9.
Chinese communication, with English translation, mailed Jan. 14, 2014 in corresponding Chinese patent application No. CN 201180042293.4.
Taiwanese communication, with English translation, issued Jan. 23, 2015 in corresponding Taiwanese patent application No. 100131553.
Australian communication issued Nov. 29, 2013 in corresponding Australian patent application No. 2011297045.
Japanese communication, with English translation, mailed Jun. 30, 2015 in corresponding Japanese patent application No. 2012-531907.
Russian communication, with English translation, mailed Jul. 1, 2015 in corresponding Russian patent application No. RU 2013114481.
Russian communication, with English translation, dated May 30, 2016 in corresponding Russian patent application No. 2013114481.
Russian communication, with English translation, dated Jun. 8, 2016 in corresponding Russian patent application No. 2013114481.

(Continued)

Primary Examiner — Michael B Pallay
(74) Attorney, Agent, or Firm — Nields, Lemack & Frame, LLC

(57) ABSTRACT

[Problem] There has been a requirement for a process for producing a pharmaceutical preparation that is obtained by encapsulating a uniform poorly water-soluble drug in a block copolymer, and dissolves immediately with an addition of water, and does not contain residues of organic solvents.
[Solution] Provided is a method for producing a drug-block copolymer composite, the method comprising: mixing a poorly water-soluble drug and a block copolymer including a hydrophilic segment and a hydrophobic segment bonded together, in one or more non-aqueous solvents; optionally heating the mixture as necessary; and spray-drying the resulting mixture liquid.

11 Claims, No Drawings

(56) References Cited

OTHER PUBLICATIONS

Kumar et al., "Nano and Microparticles as Controlled Drug Delivery Devices," Journal of Pharmacy and Pharmaceutical Sciences, vol. 3, No. 2, pp. 234-258, 2000.

Russian communication, with English translation, dated Oct. 29, 2015 in corresponding Russian patent application No. 2013114481.

* cited by examiner

PROCESS FOR PRODUCING DRUG-BLOCK COPOLYMER COMPOSITE AND PHARMACEUTICAL PREPARATION CONTAINING SAME

TECHNICAL FIELD

The present invention relates to a method for producing a composite of a poorly water-soluble drug and a block copolymer including a hydrophilic segment and a hydrophobic segment bonded together, by spray drying a non-aqueous liquid containing the poorly water-soluble drug and block copolymer in a state of solution and/or dispersion. Furthermore, the present invention relates to a method for producing a pharmaceutical preparation containing the composite.

BACKGROUND ART

There are known compositions which form polymer micelles as a drug carrier, by encapsulating a poorly-water-soluble drug in a block copolymer which includes a hydrophilic segment and a hydrophobic segment bonded together, and methods for producing the composition. Particularly, block copolymers which comprised of a polyethylene glycol derivative as a hydrophilic segment and a polyamino acid or a derivative thereof as a hydrophobic segment, have a nature to form self-associating micelles easily in water with relative ease. Therefore, such block copolymers are used as carriers for drug delivery systems (Patent Literature 1).

To make a such composition, there have been also known in the art a method comprising once dissolving such a block copolymer and a poorly water-soluble drug in an organic solvent, then distilling off the solvent, and dispersing the residue in water (see Patent Literature 2 and Patent Literature 3).

A method for powderizing a water-soluble drug by spray drying is disclosed in Patent Literature 4. Also, a method for powderizing a melted polymer by spray cooling is disclosed in Patent Literature 5.

CITATION LIST

Patent Literatures

Patent Literature 1: JP2777530B2
Patent Literature 2: JP3615721B2
Patent Literature 3: JP2003-342168A.
Patent Literature 4: JP11-114027A.
Patent Literature 5: JP 7-041154B

SUMMARY OF INVENTION

Technical Problem

On the occasion of preparing a polymer micelle in an aqueous solution, which contains a poorly water-soluble drug encapsulated by a block copolymer, in general, a poorly water-soluble drug is once dissolved in a volatile good solvent, the solution is dispersed in water with block copolymer, and the organic solvent is then removed by conventional methods such as dialysis methods or liquid drying methods, because it is difficult to uniformly disperse the poorly water-soluble drug in water. However, in these methods, it is also difficult to remove the residual organic solvents completely. The residual organic solvents will lead to a serious problem when it remains in the pharmaceutical compositions. There has been a necessity to reduce their residual amounts as low as possible in pharmaceutical compositions.

Furthermore, also disclosed are methods of dissolving a poorly water-soluble drug and a block copolymer in a volatile good solvent for the both, subsequently removing the solvent, thereby obtaining a dried, composite of the poorly water-soluble drug and the block copolymer, and dispersing the above dried composite in water to obtain a polymer micelle. However, depending on the nature of the composite to be obtained, the composite may became too hard to disperse in water without a large mechanical force, or the two components may have different ties in the solvent, causing concentration deflection during a drying process. Consequently, it has been difficult to obtain a uniform quality composite.

There has been widely known in the art food processing a method of obtaining a dry solid material by a conventional spray drying process. In general, drying is carried out in an atmosphere or environment, at a temperature close to tile boiling point of the solvent, to be used. However, pharmaceutical substances, which are generally unstable in heat, cause increases in the amount of impurities when the substances are exposed in such a high temperature environment even for a short time. Therefore, the spray drying method has been difficult to apply to such heat-sensitive pharmaceutical substances. There are known some methods of spray drying in a limited environment at a relatively low temperature; however, in the case that a composition contains a polymer component having a relatively low melting point, it has been difficult to obtain dried solid materials due to thermo-plasticity of the polymer component.

In regard to certain kinds of polymer compounds, some methods for obtaining small particles by spray-cooling (i.e., a heat-molten material of such a polymer compound is sprayed and cooled) have been published. However, in order to obtain a molten material, with a certain viscosity applicable for spraying, relatively high temperature heating is needed, and it is difficult to apply this heating to prepare a composition containing pharmaceutical substances. Furthermore, a highly viscose compound is not suitable for spraying. Depending on the intrinsic properties of the polymer compound, the polymer compound may not be sufficiently solidified even if it sprayed in a chilled environment to be rapidly cooled, and may also be sticky like a cotton candy, so that the polymer compound may become inapplicable.

Solution to Problem

The present inventors have conducted a thorough investigation in order to solve the problems described above. As a result, the inventors have found a novel spray drying method comprising dissolving a poorly water-soluble drug and a block copolymer into a volatile non-aqueous solvent; optionally heating the mixture liquid to a tolerable extent; and spraying the liquid into a relatively low temperature environment to sufficiently remove the non-aqueous solvent, whereby the solidification of the block copolymer is also promoted by the vaporization heat of the solvent. The present method can carry out a spray drying in such a low temperature environment in which the solvent is not easily removed sufficiently under the conventional spray drying conditions. In addition, the present inventors have succeeded in obtaining a powder composite having high uniformity and high water-affinity which contain a poorly water-soluble drug and a block copolymer in fusion.

That is, the present invention relates to the following aspects (1) to (15).

(1) A method for producing a drug-block copolymer composite, the method comprising: mixing a poorly water-soluble drug and a block copolymer including a hydrophilic segment and a hydrophobic segment bonded together, in one or more non-aqueous solvent (s); optionally heating the resulting mixture liquid; and spray-drying the mixture liquid.

(2) The method according to item (1), wherein the mixture liquid containing the poorly water-soluble drug and the block copolymer is heated, and the mixture liquid is spray-dried in a gas flow environment maintained at a temperature lower than or equal to the melting point of the block copolymer.

(3) The method according to item (1) or (2), wherein the mixture liquid containing the poorly water-soluble drug and the block copolymer is heated to a temperature of 25° C. or higher.

(4) The method according to item (1) or (2), wherein the mixture liquid containing the poorly water-soluble drug and the block copolymer is heated to a temperature of 35° C. or higher.

(5) The method according to item (2), wherein the gas flow environment employed for the spray-drying is at a temperature of 40° C. or lower.

(6) The method according to item (2), wherein the gas flow environment employed for the spray-drying is at a temperature of 20° C. or lower.

(7) The method according to any one of items (1) to (6), wherein the proportion of components other than the non-aqueous solvent in the mixture liquid containing the poorly water-soluble drug and the block copolymer is 10% by mass or more relative to the total mass of the mixture liquid.

(8) The method according to any one of items (1) to (7), wherein the poorly water-soluble drug is a poorly water-soluble anticancer agent, antibiotic substance, anti-rheumatic agent, or antibacterial agent.

(9) The method according to any one of items (1) to (8), wherein the poorly water-soluble drug is a poorly water-soluble anticancer agent.

(10) The method according to any one of items (1) to (9) wherein the hydrophilic segment of the block copolymer is polyethylene glycol or a derivative of polyethylene glycol, and the hydrophobic segment is a derivative of polyaspartic acid or polyglutamic acid.

(11) The method according to any one of items (1) to (10), wherein the non-aqueous solvent is an organic solvent having a boiling point of 85° C. or lower.

(12) The method according to item (11), wherein the organic solvent is one or more selected from the group consisting of ethanol, methanol, ethyl acetate, isopropanol, hexane, chloroform, dichloromethane, acetone, acetonitrile, and tetrahydrofuran.

(13) The method according to any one of items (1) to (12), wherein the mixture liquid containing the poorly water-soluble drug and the block copolymer further contains one or more compounds selected from the group consisting of sugars, sugar alcohols, inorganic salts, and surfactants.

(14) The method according to item (13), wherein the surfactant is polyethylene glycol, polysorbate, poly (oxyethylene) hydrogenated castor oil, or a mixture thereof.

(15) A pharmaceutical preparation comprising the drug-block copolymer composite obtained by the method according to any one of items (1) to (14).

Advantageous Effects of Invention

According to the present embodiment, the composite of a poorly water-soluble drug and a block copolymer including a hydrophilic segment and a hydrophobic segment that are bonded together, may be obtained continuously with sufficient uniformity and high water-affinity. Furthermore, since the composite may be obtained in the form of dry powder, the amounts of residual solvents are easily controlled. It is also possible to produce the composite aseptically in the form of dry powder by using the present method. If one may make and fill the composite aseptically as received, the composite may be used to prepare as an aseptic injectable preparation which is dissolved by a suitable solution at site. Furthermore, the composite may also be used as an intermediate material during manufacturing processes, subsequently prepared as an injection solution or a lyophilized injectable preparation.

DESCRIPTION OF EMBODIMENTS

The present method includes the acts of mixing a poorly water-soluble drug with a block copolymer including a hydrophilic segment and a hydrophobic segment that are bonded together in one or more non-aqueous solvents; heating the mixture; and spray-drying the resulting mixture liquid.

The term of "drying" is meant to also include removing non-aqueous solvents by evaporation.

The spray drying process in the present production method is carried out by spraying into dried gas flow the mixture liquid which includes a non-aqueous solvent dissolved and/or dispersed the block copolymer and a poorly-water-soluble drug. The mixture liquid may preferably be heated to form a solution. The mixture liquid may preferably be sprayed into a blowing gas environment at a temperature lower than or equal to the melting point of the block copolymer.

The temperature at which the mixture is heated may vary depending on the properties such as melting point of the block copolymer contained therein, or on the boiling point of the non-aqueous solvent used. For instance, the temperature may preferably be from 25° C. to 95° C., and more preferably from 35° C. to 80° C. However, a temperature condition which is not in that range may also be employed.

The temperature of the blowing gas flow environment, in which the mixture liquid is sprayed, may vary depending on the melting point of the block copolymer contained therein. The temperature may preferably be from 0° C. to 40° C., and more preferably from 0° C. to 20° C. However, spraying may also be carried out at a temperature which is not in that range.

The amount of components other than the non-aqueous solvent that is contained in the mixture liquid is not particularly limited, but the amount may preferably be from 1% by mass to 00% by mass, and more preferably from 10% by mass to 70% by mass.

There are no particular limitations on the process of spraying liquid as long as it is a method of exposing the mixture as microscopic droplets into blowing gas flow environment. However, examples of the method may include, but are not limited to, a binary fluid spray nozzle method, a rotary atomizer method, and a dropping method.

The poorly water-soluble drug that is used in the present method may be a pharmaceutical substances having a solubility in 1 mL of water of 1 mg or less at room, temperature (15° C. to 25° C.). The drug may include, but not limited to, pharmaceutical substances such as anticancer agents, antibiotic substances, anti-rheumatic agents and antibacterial agents. Examples of the drug may include, but not limited to, paclitaxel, docetaxel, cisplatin, doxorubicin, daunorubicin, camptothecin, topotecan, roxithromycin, methotrexate, etoposide, vincristine sulfate, amphotericin B, polyene-based antibiotic substances, nystatin, and prostaglandins.

The non-aqueous solvent used in the present method may preferably be a non-aqueous solvent which is liquid at room temperature, and a non-aqueous solvent having a boiling point of 95° C. or lower is particularly preferred, while a non-aqueous solvent having a boiling point of 85° C. or lower is more preferred. Examples of the solvent may include, but not limited to, organic solvents such as ethanol, methanol, ethyl acetate, isopropanol, hexane, chloroform, dichloromethane, acetone, acetonitrile, and tetrahydrofuran. Among these, one kind may be used, or two or more kinds may be used in combination.

The block copolymer used in the present method includes a hydrophilic segment and a hydrophobic segment that are bonded together, and may preferably be an AB type block copolymer. Such a block copolymer may be a polymer material which forms polymer micelles that are capable of maintaining a poorly water-soluble drug in an aqueous solvent in a state of being applicable as an injectable preparation. Examples of the hydrophilic segment may include, but not limited to polyethylene glycol and derivatives thereof. Examples of the hydrophobic segment may include, but not limited to polyaspartic acid and derivatives thereof, and polyglutamic acid and derivatives thereof.

An example of the block copolymer may be a compound represented by the formula:

of the sugar alcohols may include, but not limited to, mannitol, xylytol, and sorbitol. Examples of the inorganic salts may include, but not limited to hydrochloric acid salts, carbonic acid salts, and phosphoric acid salts. Examples of the surfactants may include, but are not limited to, polyethylene glycol, polysorbate, and poly(oxyethylene) hydrogenated castor oil.

The drug-block copolymer composite obtained by the present method may preferably be such that the poorly water-soluble drug may be dissolved in the block copolymer, or the composite may form self-associating micelles in water. In the case of the composite forms micelles, the particle size may preferably be around 30 nm to 150 nm as measured by using a dynamic light scattering method.

A pharmaceutical preparation containing the drug-block copolymer composite that is obtained by the present method is also included in the scope of present invention. Furthermore, the drug-block copolymer composite may also be used as an intermediate product for pharmaceutical product during a manufacturing processes, and the composite may be further subjected to processes such as dissolution, sterilization, and lyophilization. Moreover, an aseptic dry powder that is to be obtained by spray drying the drug-block copolymer composite as an aseptic solution and/or dispersion liquid in an aseptic environment, may be used directly as an injectable preparation.

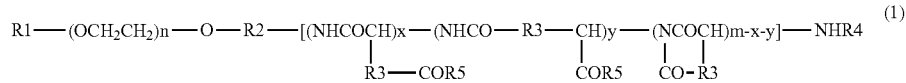

(1)

wherein R1 is methyl or ethyl group; R2 is ethylene or trimethylene group; R3 is methylene group; R4 is formyl, acetyl, or propionyl group; R5 is one or two substituents selected from the group consisting of benzyloxy, phenylethoxy, phenylpropoxy, phenylbutoxy, phenylpentyloxy, and —N(R6)-CO—NHR7 group, wherein R6 and R7, which may be identical with or different from each other, each represent ethyl, isoproyl, cyclohexyl, or dimethylaminopropyl group; n represents 20 to 500; m represents 10 to 100; x represents 0 to 100; y represents 0 to 100, provided that the sum of x and y is 1 or more but is not greater than m; and the number of benzyloxy, phenylethoxy, phenylpropoxy, phenylbutoxy, or phenylpentyloxy group among the substituents for R5 is from (0.15 m) to (0.70 m) on the average.

Such a block copolymer may be produced by, for example, the conventional production methods described in a conventional publication such as Patent Literature 1 above, JP 6-206015 A, and WO 2006/033296 A, or methods applying the production methods, but the production method is not intended to be limited to those conventional production methods.

The melting point of the block copolymer obtained in this manner may approximately be 30° C. to 70° C.

The mixture liquid that is used in the present method may also contain one or more components selected from sugars, sugar alcohols, inorganic salts, and surfactants, in addition to the block copolymer and the poorly water-soluble drug described above. Examples of the sugars may include, but not, limited to, glucose, saccharose, lactose, sucrose (e.g. white soft sugar), trehalose, maltose, and fructose. Examples

EXAMPLES

Hereinafter, the present invention will be described in more detail by way of Examples. The present invention is not intended to be limited to these Examples.

SEM (scanning electron microscopy) observation was carried out by using a scanning electron microscope (JSM-6060 manufactured by JEOL, Ltd.).

Example 1

30 parts by weight of paclitaxel, which is a poorly water-soluble drug, and 100 parts by weight of a block copolymer (melting point: 50° C. to 57° C.) including polyethylene glycol-polyaspartic acid derivative that were bonded together, which was obtained by the method described in WO 2006/033296 A, were dissolved in ethanol (boiling point: 79.3° C.) such that the content would be 20% by mass. The temperature of the liquid was adjusted to 45° C. This liquid was spray dried in a gas flow environment at an inlet temperature of 15° C., by using a spray drying experimental unit (B-290 manufactured by Nihon Buchi K.K.). The dried product thus obtained had a particle size of about 10 μm as measured by SEM observation.

Example 2

30 parts by weight of paclitaxel, which is a poorly water-soluble drug, and 100 parts by weight of the block copolymer which used the polyethylene glycol-polyaspartic acid derivative described in Example 1, were dissolved in ethanol such that the solids content would be 30% by mass.

The temperature of the liquid was adjusted to 45° C. This liquid was spray dried in a gas flow environment at an inlet temperature of 15° C., by using a spray drying experimental unit (B-290 manufactured by Nihon Buchi K.K.). The dried product thus obtained had a particle size of about 10 μm as measured by SEM observation.

Example 3

30 parts by weight of paclitaxel, which is a poorly water-soluble drug, and 100 parts by weight of the block copolymer which used the polyethylene glycol-polyaspartic acid derivative described in Example 1, were dissolved in ethanol such that the solids content would be 20% by mass. The temperature of the liquid was adjusted to 40° C. This liquid was spray dried in a gas flow environment at an inlet temperature of 10° C., by using a spray drying experimental unit (B-290 manufactured by Nihon Buchi K.K.). The dried product thus obtained had a particle size of about 10 μm as measured by SEM observation.

Example 4

Further, 200 parts by weight of PEG (polyethylene glycol 4000) was added to 30 parts by weight of paclitaxel, which is a poorly water-soluble drug, and 100 parts by weight of the block copolymer which used the polyethylene glycol-polyaspartic acid derivative described in Example 1, and the mixture was dissolved in ethanol such that the content would be 30% by mass. The temperature of the liquid was adjusted to 45° C. This liquid was spray dried in a gas flow environment at an inlet temperature of 20° C., by using a spray drying experimental unit (B-290 manufactured by Nihon Buchi K.K.). The dried product thus obtained had a particle size of about 10 μm as measured by SEM observation.

Example 5

30 parts by weight of docetaxel, which is a poorly water-soluble drug, and 100 parts by weight of the block copolymer which used the polyethylene glycol-polyaspartic acid derivative described in Example 1, were dissolved in ethanol such that the solids content would be 20% by mass. The temperature of the liquid was adjusted to 40° C. This liquid was spray dried in a gas flow environment at an inlet temperature of 15° C., by using a spray drying experimental unit (B-290 manufactured by Nihon Buchi K.K.). The dried product thus obtained had a particle size of about 10 μm as measured by SEM observation.

Comparative Example 1

30 parts by weight of paclitaxel, which is a poorly water-soluble drug, and 100 parts by weight of the block copolymer which used the polyethylene glycol-polyaspartic acid derivative described in Example 1, were pulverized and mixed in a mortar.

Comparative Example 2

30 parts by weight of paclitaxel, which is a poorly water-soluble drug, was dissolved in ethanol, and the solution was mixed with 100 parts by weight of the block copolymer which used the polyethylene glycol-polyaspartic acid derivative described in Example 1, at a liquid temperature of 15° C. This liquid was subjected to vacuum drying while the liquid temperature was maintained at 15° C., and thus a white-pale yellow powder was obtained.

Test Example

Measurement of Polymer Micelle Particle Size

Observation was made on the dispersion performance of the composites obtained in Examples 1 to 5, and the compositions obtained in Comparative Examples 1 and 2. The composites and the comparative compositions were respectively dispersed in water for injection, and stirred with an Ultra-Turrax mixer. The average particle size of the polymer micelle solutions thus obtained was measured with a particle size analyzer (ELS-Z2 manufactured by Otsuka Electronics Co., Ltd.) utilizing a dynamic light scattering method. The results are presented in Table 1.

TABLE 1

| | Solids content | Spray liquid temperature | Inlet temperature | Presence of PEG addition | Average particle size |
|---|---|---|---|---|---|
| Example 1 | 20% | 45° C. | 15° C. | no | 73.7 nm |
| Example 2 | 30% | 45° C. | 15° C. | no | 64.1 nm |
| Example 3 | 20% | 40° C. | 10° C. | no | 71.5 nm |
| Example 4 | 30% | 45° C. | 20° C. | YES | 81.5 nm |
| Example 5 | 20% | 40° C. | 15° C. | no | 71.7 nm |
| Comparative Example 1 | — | — | — | — | Not dispersed |
| Compartive Example 2 | — | — | — | — | 167.6 nm |

The drug block copolymer composites of Examples 1 to had satisfactory dispersion performance, and as is obvious from these results, the average particle sizes as micelles are also in a suitable range. On the other hand, the comparative composition of Comparative Example 1 was such that the drug was not dispersed, and it is difficult to use the composition as a pharmaceutical preparation. In regard to the comparative composition of Comparative Example 2, the drug was dispersed, but the dispersibility or dispersed appearance is not suitable for an injectable preparation. Furthermore, the average particle size was also large.

The invention claimed is:

1. A method for producing a drug-block copolymer composite comprising a poorly water-soluble drug and a block copolymer including a hydrophilic segment and a hydrophobic segment bonded together, wherein the hydrophilic segment is polyethylene glycol or a derivative of polyethylene glycol, and the hydrophobic segment is a derivative of polyaspartic acid or a derivative of polyglutamic acid, the method comprising:
   mixing the poorly water-soluble drug and the block copolymer in one or more non-aqueous solvents;
   heating the mixture; and
   spray-drying the resulting mixture liquid in a gas flow environment maintained at a temperature lower than or equal to the melting point of the block copolymer, wherein the gas flow environment employed for the spray-drying is at a temperature of 20° C. or lower,
   wherein the drug-copolymer composite produced by the method forms micelles in water, and said micelles have an average particle size of about 30 nm to 150 nm as measured by using a dynamic light scattering method.

2. The method according to claim 1, wherein the mixture liquid containing the poorly water-soluble drug and the block copolymer is heated to a temperature of 25° C. or higher.

3. The method according to claim 1, wherein the mixture liquid containing the poorly water-soluble drug and the block copolymer is heated to a temperature of 35° C. or higher.

4. The method according to any one of claims 1 or 2, wherein the proportion of components other than the non-aqueous solvent in the mixture liquid containing the poorly water-soluble drug and the block copolymer is 10% by mass or more relative to the total mass of the mixture liquid.

5. The method according to claim 1, wherein the poorly water-soluble drug is a poorly water-soluble anticancer agent, antibiotic substance, anti-rheumatic agent, or antibacterial agent.

6. The method according to claim 1, wherein the poorly water-soluble drug is a poorly water-soluble anticancer agent.

7. The method according to claim 1, wherein the non-aqueous solvent is an organic solvent having a boiling point of 85° C. or lower.

8. The method according to claim 7, wherein the organic solvent is one or more selected from the group consisting of ethanol, methanol, ethyl acetate, isopropanol, hexane, chloroform, dichloromethane, acetone, acetonitrile, and tetrahydrofuran.

9. The method according to claim 1, wherein the mixture liquid containing the poorly water-soluble drug and the block copolymer, further contains one or more compounds selected from the group consisting of sugars, sugar alcohols, inorganic salts, and surfactants.

10. The method according to claim 9, wherein the surfactant is polyethylene glycol, polysorbate, poly(oxyethylene) hydrogenated castor oil, or a mixture thereof.

11. A pharmaceutical preparation comprising the drug-block copolymer composite obtained by the method according to claim 1.

* * * * *